US012489262B2

(12) United States Patent
Glaser et al.

(10) Patent No.: US 12,489,262 B2
(45) Date of Patent: Dec. 2, 2025

(54) MEDICAL DEVICE SYSTEM WITH REMOVABLE CONNECTOR

(71) Applicant: Boston Scientific Scimed, Inc., Maple Grove, MN (US)

(72) Inventors: Steven Glaser, Cambridge, MA (US); Ryan A. Foss, Gorham, ME (US); Daniel J. Pappalardo, Sidney, ME (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 298 days.

(21) Appl. No.: 18/162,984

(22) Filed: Feb. 1, 2023

(65) Prior Publication Data

US 2023/0253746 A1 Aug. 10, 2023

Related U.S. Application Data

(60) Provisional application No. 63/308,164, filed on Feb. 9, 2022.

(51) Int. Cl.
*H01R 31/06* (2006.01)
*A61B 1/00* (2006.01)
(Continued)

(52) U.S. Cl.
CPC ....... *H01R 31/065* (2013.01); *A61B 1/00124* (2013.01); *H01R 13/6272* (2013.01);
(Continued)

(58) Field of Classification Search
CPC .............. H01R 31/065; H01R 13/6272; H01R 13/6275; H01R 12/737; A61B 1/00124
(Continued)

(56) References Cited

U.S. PATENT DOCUMENTS

| | | | |
|---|---|---|---|
| D297,763 S | 9/1988 | Daynes | |
| D400,249 S | 10/1998 | Holubar et al. | |

(Continued)

FOREIGN PATENT DOCUMENTS

| | | |
|---|---|---|
| CN | 308441604 | 1/2024 |
| EP | 1927313 A1 | 6/2008 |

(Continued)

OTHER PUBLICATIONS

Boston Scientific's LithoVue Elite System gets FDA 51 0(k) clearance, [online]. medicaldevice-network.com, Feb. 6, 2023 [retrieved on Apr. 28, 2023]. Retrieved from the Internet: <URL: https://www.medicaldevice-network.com/news/boston-scientific-lithovue-elite-system/> (Year: 2023).

(Continued)

*Primary Examiner* — Gary F Paumen
(74) *Attorney, Agent, or Firm* — Bookoff McAndrews, PLLC

(57) ABSTRACT

Aspects of the disclosure relate to devices, systems, and methods for connecting or removing one or more interposer assemblies from a controller, replacing a used interposer assembly with a new interposer assembly, and connecting or removing a medical device from such an interposer assembly. The one or more interposer assemblies for connecting the medical device to a controller may comprise a housing defining a front-facing socket for removably receiving a connector of the medical device, and at least one electrical connector on a rear face of the housing, the at least one electrical connector for removable connection to the controller.

19 Claims, 7 Drawing Sheets

(51) Int. Cl.
*H01R 12/73* (2011.01)
*H01R 13/627* (2006.01)

(52) U.S. Cl.
CPC ....... *H01R 13/6275* (2013.01); *H01R 12/737* (2013.01); *H01R 2201/12* (2013.01)

(58) Field of Classification Search
USPC ........................................ 439/327, 76.1, 676
See application file for complete search history.

(56) References Cited

U.S. PATENT DOCUMENTS

| | | | | |
|---|---|---|---|---|
| D413,879 | S | 9/1999 | Wu | |
| D499,100 | S | 11/2004 | Neel et al. | |
| D534,654 | S | 1/2007 | Hayamizu | |
| D545,784 | S | 7/2007 | Dayan | |
| 7,514,629 | B2 * | 4/2009 | Sasaki | H02G 3/086 361/752 |
| D598,551 | S | 8/2009 | Miwa et al. | |
| D612,503 | S | 3/2010 | Johnston et al. | |
| 7,686,638 | B2 * | 3/2010 | Boyd | H01R 13/6272 439/352 |
| 7,690,925 | B2 * | 4/2010 | Goodman | H01R 13/2421 439/70 |
| D632,397 | S | 2/2011 | Edwards et al. | |
| D635,681 | S | 4/2011 | Edwards et al. | |
| 8,011,973 | B2 | 9/2011 | Feng et al. | |
| D662,502 | S | 6/2012 | Wesolek | |
| D666,716 | S | 9/2012 | Hayamizu | |
| 8,480,433 | B2 * | 7/2013 | Huang | H01R 13/6658 439/620.21 |
| 8,747,164 | B2 * | 6/2014 | Westman | H01R 12/91 439/60 |
| 8,814,576 | B2 * | 8/2014 | Yoshida | H01R 12/57 439/83 |
| D715,946 | S | 10/2014 | Yoshida et al. | |
| 8,882,514 | B2 * | 11/2014 | Enge | H01R 13/65912 439/76.1 |
| D733,892 | S | 7/2015 | Fries et al. | |
| D792,970 | S | 7/2017 | Shimobayashi | |
| D793,554 | S | 8/2017 | Shimobayashi | |
| D799,035 | S | 10/2017 | Shimobayashi | |
| D822,214 | S | 7/2018 | Iles et al. | |
| D844,147 | S | 3/2019 | Benedikter et al. | |
| D852,661 | S | 7/2019 | Park et al. | |
| D878,578 | S | 3/2020 | Onuma | |
| D887,559 | S | 6/2020 | Esfandiari | |
| D895,122 | S | 9/2020 | Benedikter et al. | |
| D904,622 | S | 12/2020 | Kuester et al. | |
| 10,880,994 | B2 * | 12/2020 | Aoki | H01L 24/17 |
| D908,892 | S | 1/2021 | Duignan et al. | |
| D910,567 | S | 2/2021 | Eckstein et al. | |
| 10,911,649 | B2 | 2/2021 | Henley et al. | |
| D926,314 | S | 7/2021 | Hayamizu | |
| 11,075,481 | B1 | 7/2021 | Zou | |
| D948,512 | S | 4/2022 | Tsao et al. | |
| D965,779 | S | 10/2022 | Behrendt et al. | |
| D966,509 | S | 10/2022 | Behrendt et al. | |
| 11,471,042 | B2 | 10/2022 | Shampine et al. | |
| D1,042,331 | S | 9/2024 | Jones et al. | |
| 2008/0207028 | A1 | 8/2008 | Schutz | |
| 2013/0252444 | A1 * | 9/2013 | Keswani | H01R 13/6658 439/76.1 |
| 2016/0351526 | A1 * | 12/2016 | Boyd | H01L 24/75 |
| 2017/0303772 | A1 | 10/2017 | Shimobayashi | |
| 2018/0076588 | A1 * | 3/2018 | Torres | H01R 12/7076 |
| 2018/0217340 | A1 * | 8/2018 | Wong | G02B 6/3893 |
| 2020/0021930 | A1 | 1/2020 | Iswanto et al. | |
| 2020/0106217 | A1 | 4/2020 | Liu et al. | |
| 2021/0066860 | A1 | 3/2021 | Yang | |
| 2022/0265949 | A1 | 8/2022 | Davidson et al. | |
| 2022/0328998 | A1 | 10/2022 | Droesbeke et al. | |
| 2023/0035044 | A1 | 2/2023 | Yang et al. | |
| 2023/0094703 | A1 | 3/2023 | Zhao et al. | |

FOREIGN PATENT DOCUMENTS

| | | |
|---|---|---|
| FR | 3109289 A1 | 10/2021 |
| GB | 6417610 | 1/2025 |
| JP | D1788842 | 1/2025 |
| WO | D223766-001 | 8/2023 |
| WO | D223766-002 | 8/2023 |
| WO | D223766-003 | 8/2023 |

OTHER PUBLICATIONS

Radiofrequency Ablation Generator, gobizkorea.com, [online], [site visited Apr. 28, 2023], Available from internet, URL: https://www.gobizkorea.com/mobile/mobileGoodsDetail.do?goods_no=GS2021122911533 (Year: 2023).
Dental implantology micromotor control unit NS-UD300, medicalexpo.com, [online], [site visited Apr. 28, 2023], Available from internet, URL: https://www.medicalexpo.com/prod/jiangsu-nuoxen-medical-technology-co-ltd/product-299025-983467.html (Year: 2023).
International Search Report and Written Opinion issued in International Application No. PCT/US2023/061747, issued May 8, 2023 (12 pages).
PENTAX Medical to launch new premium video processor and endoscope series [online]. pentaxmedical.com, Jan. 16, 2023 [retrieved on Jul. 24, 2023]. Retrieved from the Internet: <URL:https://www.pentaxmedical.com/pentax/en/92/1/PENTAX-Medical-to-launch-new-premium-video-processor-and-endoscope-series> (Year: 2023).
"Medi|Slice Low-cost Interconnects for Limited-use Applications," Amphenol Alden Products, https://www.amphenolalden.com/products-solutions/Medi-Slice-Interconnects, retrieved Apr. 12, 2024.
Handheld patient monitor. By Spacelabs Healthcare. Dated Sep. 5, 2019. Found online [May 23, 2025]. https://www.medicalexpo.com/prod/spacelabs-healthcare/product-70868-443964.html, (Year: 2019).
LithoVue Elite System. By Boston Scientific Corporation. Dated Sep. 17, 2023. Found online [May 23, 2025]. https://www.bostonscientific.com/en-US/products/Ureteroscopes/LithoVue-Elite.html, (Year: 2023).
XPS Nexus console. By Trent Medical Systems. Dated Date Not Available. Found online [May 23, 2025]. https://trentmedical.in/product/xps-nexus-console/, (Year: 2025).

* cited by examiner

MEDICAL DEVICE SYSTEM WITH REMOVABLE CONNECTOR

CROSS-REFERENCE TO RELATED APPLICATIONS

This application claims the benefit of priority under 35 U.S.C. § 119 from U.S. Provisional Application No. 63/308,164, filed Feb. 9, 2022, which is incorporated by reference herein in its entirety.

TECHNICAL FIELD

This disclosure generally relates to medical systems, devices, and related methods for interchanging one or more connectors to a controller. Such a connector enables a medical device, such as a scope, to connect to the controller.

BACKGROUND

Current medical device systems generally include a medical device, such as a scope, and a controller. The scope may be, for example, an endoscope, duodenoscope, gastroscope, bronchoscope, or any other scope commonly used in the field. The scope may connect to the controller by attaching a connector of the scope to a plug or port in the controller. A camera and other associated electronics in the scope may transmit an image from visualization components of the scope to the controller through an electrical connection within the port. The scope is typically inserted to the port just prior to a procedure and removed after the procedure.

While such controllers have proven to be acceptable for their intended applications, they are associated with limitations. For example, scopes are repeatedly inserted and removed from the port over the course of the controller's shelf life. This may result in wear and tear of the controller port. As the connection between the scope and controller wears, the opportunity for partial or intermittent operation of the scope increases. Partial or intermittent operation of the scope can result in degraded performance of the scope's visualization and/or light output and may result in momentary or permanent visualization loss during a procedure. This can result in return of the controller to the manufacturer for repair or replacement.

These concerns may increase the duration, costs, and risks of medical procedures that require a scope and a controller. The systems, devices, and methods of this disclosure may rectify one or more of the deficiencies described above or address other aspects of the art.

SUMMARY

Examples of the disclosure relate to, among other things, systems, devices, and methods for performing one or more medical procedures using a controller having a replaceable interposer assembly. Each of the examples disclosed herein may include one or more of the features described in connection with any of the other disclosed examples.

In one example, an interposer assembly for connecting a medical device to a controller may comprise a housing defining a front-facing socket for removably receiving a connector of the medical device, and at least one electrical connector on a rear face of the housing. The at least one electrical connector may be configured for removable connection to the controller. The interposer assembly may further comprise at least one mechanical fastener on a rear face of the housing. The at least one mechanical fastener may include a plurality of screws and enable a removable connection to the controller. Additionally, access to the at least one mechanical fastener may be through the socket of the housing. The interposer assembly may also comprise a gas discharge tube. In an exemplary interposer assembly, a circuit of the gas discharge tube may comprise a capacitor in parallel to the gas discharge tube. The circuit may also be used for an electrical connection to a ground connection within the controller.

The interposer assembly may further comprise a latch. The latch may include a protrusion for inhibiting removal of the connector of the medical device from the socket. The latch may be removable from the housing via one or more latch fasteners. The protrusion may protrude radially inward towards the socket and include a rear-facing surface for contact with the connector of the medical device. The protrusion may inhibit removal of the connector of the medical device from the socket.

In an alternative embodiment, an interposer assembly for connecting a medical device to a controller may comprise a housing defining a front-facing socket for removably receiving a connector of the medical device, and at least one electrical connector on a rear face of the housing. The housing of the interposer assembly may be a shape corresponding to a shape of a port of the controller. The medical device to be connected to the interposer assembly may include an endoscope. The at least one electrical connector of the interposer assembly may enable a removable connection to the controller. The interposer assembly may further comprise at least one mechanical fastener on a rear face of the housing. The mechanical fastener may enable a removable connection to the controller. The at least one mechanical fastener may include a plurality of screws. Access to the at least one mechanical fastener may be through the socket of the housing.

The interposer assembly may further comprise a gas discharge tube. A circuit of the gas discharge tube may comprise a capacitor in parallel to the gas discharge tube, and the circuit may be used for an electrical connection to a ground connection within the controller. The alternative embodiment of the interposer assembly may further comprise a latch including a protrusion for inhibiting removal of the connector of the medical device from the socket. The latch may be removable from the housing via one or more latch fasteners. The protrusion may protrude radially inward towards the socket and include a rear-facing surface for contact with the connector of the medical device. The protrusion may inhibit removal of the connector of the medical device from the socket.

The interposer assembly may comprise a printed circuit board assembly (PCBA) electrically connected to the at least one electrical connector. The PCBA may be removably connected to the housing via one or more PCBA connectors. A front-facing wall of the housing may include a circuit board connector for receipt of a circuit board of the connector of the medical device.

In an alternative embodiment, the interposer assembly may comprise a spring pin mount on a front-facing wall of the housing and in communication with the socket, the spring pin mount for electrical connection to the connector of the medical device.

An alternative embodiment may include a medical system comprising a controller including at least one port and an interposer assembly. The interposer assembly may be configured to be removably coupled to the controller through the at least one port and removably receive a connector of a medical device. The interposer assembly of this embodiment may include a housing that defines a front-facing socket for removably receiving the connector of the medical device. The interposer assembly may also comprise at least one electrical connector on a rear face of the housing. The at least one electrical connector may enable a removable connection to the controller.

An alternative example of this disclosure may relate to a method for connecting a medical device to a controller. The method may include inserting a connector of the medical device into a socket of an interposer assembly, the interposer assembly positioned in a port of the controller via a releasable connection.

It may be understood that both the foregoing general description and the following detailed description are exemplary and explanatory only and are not restrictive of this disclosure, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Figure 1:
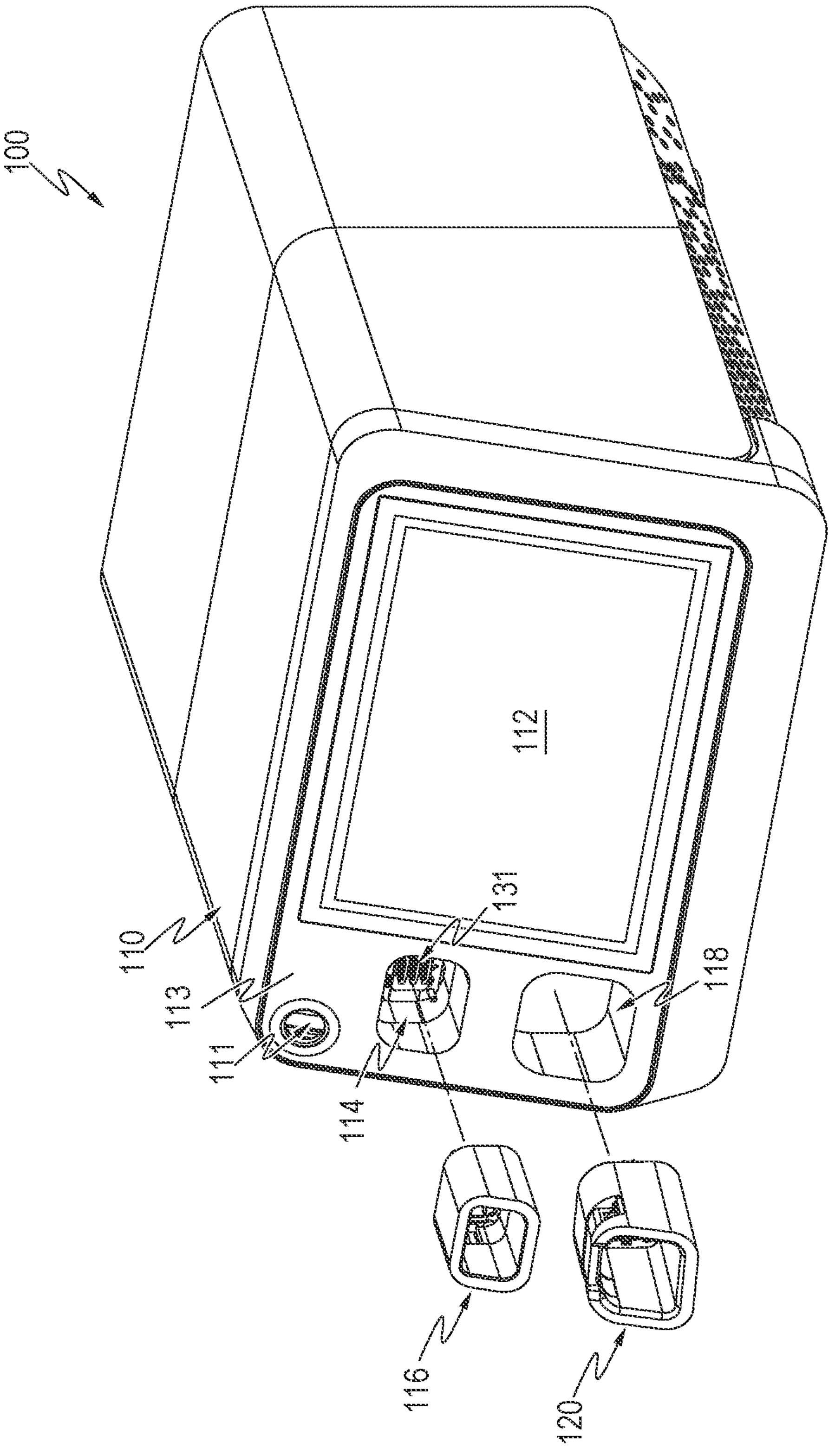
FIG. 1 illustrates a perspective view of the medical system, including a controller, a first interposer assembly, and a second interposer assembly, according to aspects of this disclosure.

Aspects of the disclosure include devices, systems, and methods for connecting or removing one or more interposer assemblies from a controller, replacing a used interposer assembly with a new interposer assembly, and connecting or removing a medical device from such an interposer assembly. The ability to easily remove an interposer assembly from a controller and replace it with a new interposer assembly can, for example, extend the lifetime of a controller, result in less service time or down time for the controller, reduce cost, increase performance of the system, and increase user satisfaction.

Current devices and methods for connecting and removing interposers are limited. For example, when a scope can no longer be connected to the controller due to wear and tear of the port within the controller, the entire controller is removed from the field and serviced. Only after the controller is repaired is it allowed to return to the field. This process can lead to inefficiencies related to patient scheduling and increased costs to the user.

There is a need therefore to be able to quickly and easily remove an inoperable or damaged interposer assembly of the controller and replace it with a new and working interposer assembly. The ability to interchange the interposer assemblies of the controller without removing the controller from the field can decrease costs and downtime of the controller and reduce difficulties associated with patient scheduling. Furthermore, the ability to not only exchange identical interposer assemblies but also to interchange interposer assemblies of different devices into the same controller enables a wider variety of devices (e.g. scopes) to be used with the same controller. For example, a first interposer assembly may be configured to accept a first scope, and a second interposer assembly may be configured to accept a different scope. These interposer assemblies, which can mate with the same controller, may be interchanged such that one controller may be used with both scopes.

Alternatively, in other embodiments, two interposer assemblies may be coupled to the same controller at the same time, as described below. Those two interposer assemblies each may be for the same device, or they may differ from one another such that two different devices may connect to the controller and be used, for example, at the same time. Additionally, the ability to remove, couple, and interchange interposer assemblies over the life of a controller enables the ability to iterate and change a scope's configuration without the need for a new controller. For instance, a newly developed scope and its connector, for example with updated imaging or lighting circuitry and components, may be designed to connect with an interposer assembly compatible with a controller already in the field.

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the subject. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may relate to systems, devices, and methods for connecting, removing, and interchanging one or more interposer assemblies from a controller in order to perform a wide variety of medical procedures using a number of different medical devices (e.g. scopes) and one controller. Various examples described herein include medical device systems comprising a multi-use medical controller, a variety of interposer assemblies that may be removably coupled to the controller, and reusable or single-use/disposable medical devices.

Embodiments of this disclosure include controllers having the ability to couple to and be removable from various interposer assemblies to which a variety of medical devices (e.g. scopes) may be connected to. Embodiments of this disclosure also include the electrical and mechanical connection of device connectors to the interposer assemblies and the electrical and mechanical connection of the interposer assemblies to the controller.

Although exemplary embodiments of this disclosure will be described with reference a controller with interchangeable interposer assemblies and corresponding medical devices, it will be appreciated that aspects of this disclosure have wide application, and thus may be suitable for use with many types of medical controllers, medical devices (such as endoscopes, bronchoscopes, colonoscopes, gastroscopes, duodenoscopes, etc.), and non-medical devices, such as borescopes. Accordingly, the following descriptions and illustrations should be considered illustrative in nature, and thus, not limiting the scope of this disclosure.

FIG. 1 illustrates an exemplary medical system 100. Medical system 100 comprises a controller 110 and at least one of a first interposer assembly 116 and/or a second interposer assembly 120, to be described further therein.

First interposer assembly 116 may be connected to controller 110 through a first port 114. Similarly, second interposer assembly 120 may be connected to controller 110 through a second port 118. Each of first port 114 and second port 118 is similarly shaped to accept first interposer assembly 116 and second interposer assembly 120, respectively. For example, first interposer assembly 116 and second interposer assembly 120 are shown to be rectangular with curved corners. Thus, each of first port 114 and second port 118 are rectangular with curved corners. However, the shapes of first interposer assembly assemblies 116 and first port 114, and similarly second interposer assembly 120 and second port 118, are not limited to rectangular shapes and may be a variety of sizes and shapes (i.e. square, circular, ovular, hexagonal, etc.).

The number of first port 114 and/or second port 118 may vary, as well. For example, controller 110 may include just one first port 114 or one second port 118. Alternatively, controller 110 may include two or more first ports 114, two or more second ports 118, or any combination of first port 114 and second port 118. For example, controller 110 may include one first port 114 and two second ports 118. Additionally or alternatively, the location of first port 114 and second port 118 may vary. For example, first port 114 and/or second port 118 may be located on a front face 113 of the controller 110 (as shown). Alternatively, one or more first port 114 and/or second port 118 may be located on a back face (not shown) and/or a side face of controller 110 (e.g., a left or right side face of controller 110).

In an alternative embodiment, first port 114 and/or second port 118 may be located on different sides of controller 110. For example, first port 114 may be located on front face 113 of controller 110 and second port 118 may be located on the side or back face of controller 110, or vice versa. First port 114 and second port 118 enable a mechanical connection and an electrical connection between first interposer assembly 116 and second interposer assembly 120, respectively, and controller 110, for example, such that first interposer assembly 116 and/or second interposer assembly 120 are able to electrically communication with controller 110. Controller 110 comprises electronics and components necessary to facilitate the electrical connection between first interposer assembly 116 or second interposer assembly 120 and controller 110.

Controller 110 may further comprise a power button 111 and a display screen 112. The shape, size, and/or location of power button 111 is not limited to a circular button on front face 113 of controller 110, as shown. For example, power button 111 may be located on the back face of controller 110 and/or may be a switch, knob, trigger, or any other control commonly known in the art. Additionally, display screen 112 may be a touchscreen or a simple screen (i.e. non-touchscreen). If display screen 112 is a simple screen, one or more buttons (not shown) on controller 110 may control its functions. Controller 110 may also include additional electrical ports (i.e. HDMI, USB, VGA, etc.) (not shown) to facilitate the connection of one or more external displays (not shown), one or more power sources (e.g. an electrical plug), or other peripherals.

In alternative embodiments (not shown), controller 110 made be configured without display screen 112. In such an embodiment, controller 110 may comprise additional electrical ports (i.e. HDMI, USB, VGA, etc.) (not shown) to facilitate the connection of one or more external displays (not shown), one or more power sources (e.g. an electrical plug), or other peripherals. Controller 110 may include one or more buttons, switches, knobs, triggers, or any other control commonly known in the art to control other functions of the controller or to control a variety of functions of a connected device (e.g. illumination, imaging sensors, or other controls).

Figure 2A:
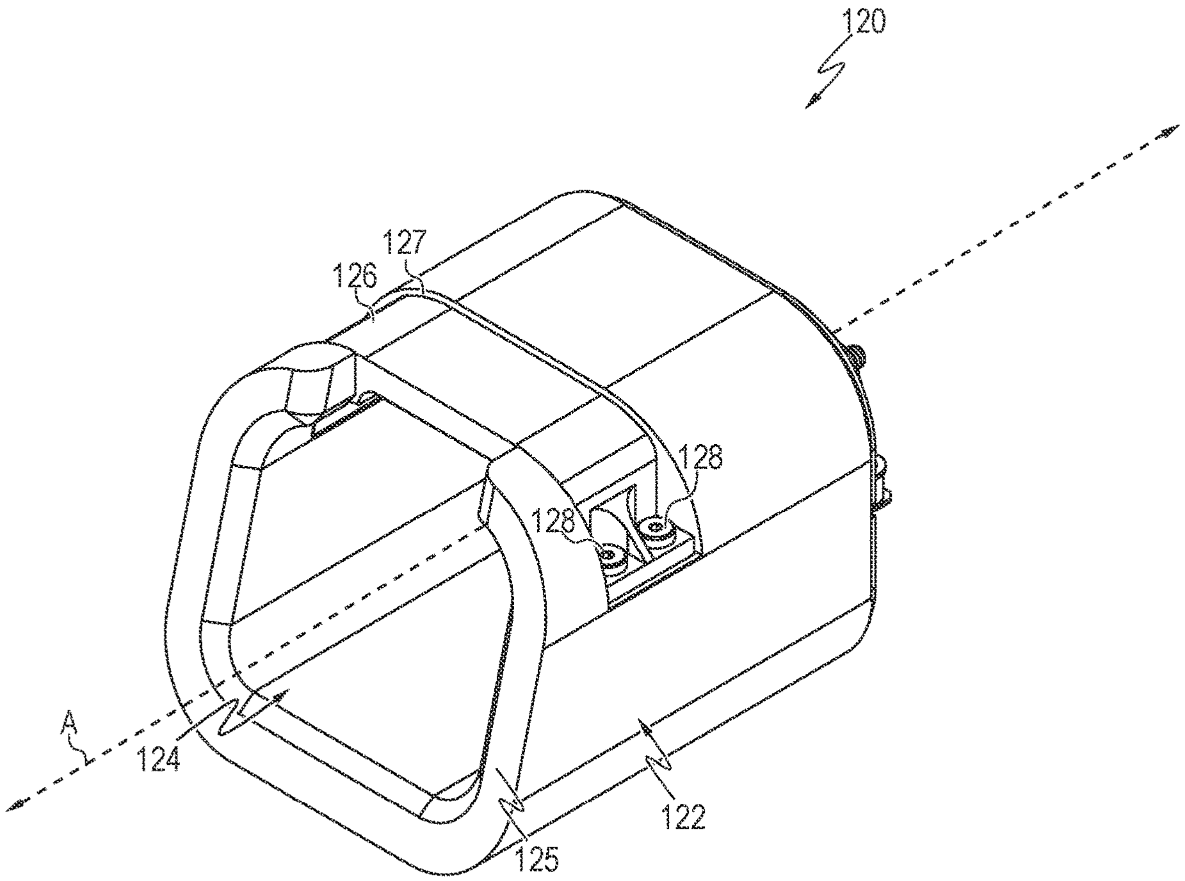
FIG. 2A illustrates a perspective view of a front of the first interposer assembly as shown in FIG. 1, according to aspects of this disclosure.

FIG. 2A shows a perspective view of the front of second interposer assembly 120. Second interposer assembly 120 is comprised of an interposer housing 122. A connector socket 124 is a space within interposer housing 122 and extends from a front face 125 of interposer housing 122, for example, along a center axis A to a socket wall 141 (shown in FIG. 2D) at a rear of interposer housing 122. Center axis A extends perpendicularly outward from socket wall 141 (shown in FIG. 2D), towards front face 125 of second interposer assembly 120. Connector socket 124 is shaped and sized to receive a similarly shaped and sized connector of a medical device (e.g. a scope), for example, as shown in FIG. 3 and to be described in further detail below.

Additionally, a latch 126 extends across a top portion of interposer housing 122, within a slot 127. Latch 126 and slot 127 are oriented perpendicular to center axis A of interposer housing 122. Latch 126 may be removably coupled to interposer housing 122 by one or more fasteners 128, for example, at each end of latch 126. One or more fasteners 128 may include screws (as shown), nails, bolts, rivets, or any other type of fastener commonly known in the art. Alternatively, latch 126 may be permanently coupled to interposer housing 122 via a glue, a press-fit, a weld, or any other means commonly known in the art. Latch 126 sits within slot 127 such that a top surface of latch 126 is flush with a top surface of interposer housing 122. As shown in FIG. 3, latch 126 mechanically fastens the connector of the medical device to second interposer assembly 120, while still allowing for a user to easily disconnect the two components. An undersurface 129 of latch 126 (shown in more detail in FIG. 3 and to be described further herein) engages a top surface of a connector tab of the inserted connector of the medical device, thereby preventing the device connector from being inadvertently removed from second interposer assembly 120.

Still referring to FIG. 2A, latch 126 and interposer housing 122 may be made of one or more biocompatible materials such as metals, polymers, or other biomaterials. For example, latch 126 and interposer housing 122 may be comprised of stainless steel or a plastic. Alternatively, latch 126 may be molded or 3D printed with a biomaterial such as a plastic, and interposer housing 122 may be machined from stainless steel. In an alternative embodiment, latch 126 may be monolithically formed with interposer housing 122.

Figure 2B:
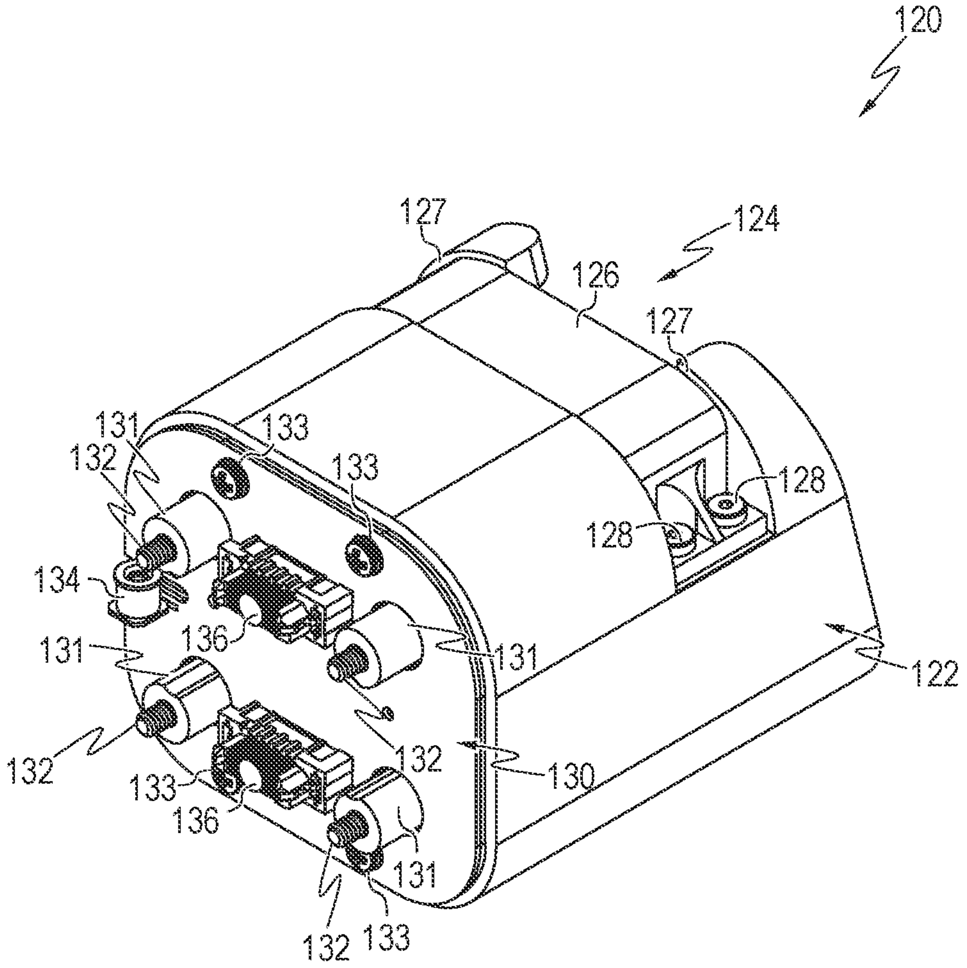
FIG. 2B illustrates a perspective view of a back of the first interposer assembly shown in FIGS. 1 and 2A, according to aspects of this disclosure.
Figure 2C:
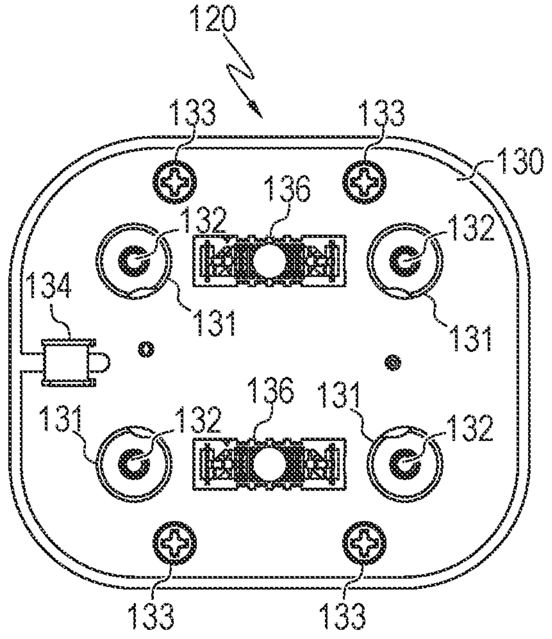
FIG. 2C illustrates a back view of the first interposer assembly shown in FIGS. 1, 2A, and 2B, according to aspects of this disclosure.

FIG. 2B is a perspective view of second interposer assembly 120, including a back wall 130, and FIG. 2C depicts an elevation, rear view of back wall 130 of second interposer assembly 120. Back wall 130 may be comprised of an interposer printed circuit board assembly (PCBA). Alternatively, back wall 130 may be a panel enclosing a PCBA, for example within second interposer assembly 120. A plurality of fasteners 133, such as, for example, screws (as shown), nails, bolts, rivets, or any other type of fastener commonly known in the art, may removably couple back wall 130 to interposer housing 122 of second interposer assembly 120. Alternatively, back wall 130 may be permanently coupled to interposer housing 122 via a glue, a press-fit, a weld, or any other means commonly known in the art.

A plurality of extensions 131 extend perpendicularly from back wall 130. A fastener 132 extends from each of the plurality of extensions 131. Each fastener 132 extending from the plurality of extensions 131 enables second interposer assembly 120 to be removably coupled to controller 110 of FIG. 1. A user may access fastener 132 through connector socket 124. The number, size, location, and type of fasteners 132 and the number, size, and shape of the extensions 131 may vary. For example, second interposer assembly 120 may include two square extensions 131 from which fasteners 132, such as captive screws, extend. In such an example, extensions 131 and fasteners 132 may be located in opposite corners of back wall 130.

One or more connectors 136 may also extend perpendicularly from back wall 130. Connectors 136 enable an electrical and/or mechanical connection between second interposer assembly 120 and controller 110 of FIG. 1. The electrical connection between second interposer assembly 120 and controller 110 enables the use of a connected device (not shown) by a user. For example, when a device is connected to second interposer assembly 120, and second interposer assembly 120 is connected to controller 110 of FIG. 1, a user may be able to control one or more electrical features of the device, such as, for example, an imaging sensor, illumination source, or other operative controls.

Second interposer assembly 120 may also include a gas discharge tube (GDT) 134 extending perpendicularly from back wall 130. GDT 134 is a type of inert gas filled tube commonly used as a high-voltage, high-energy, surge protection device in electronics. In particular, GDT 134 may be used as a protective device in a medical system, including, for example, medical system 100 shown in FIG. 1, for use with high-frequency electrosurgical generators (not shown). If a device is comprised of one or more conductive components, for example, such as an articulating metal elevator in a distal tip of the device (not shown), and the device is subsequently connected to second interposer assembly 120, the output of a high frequency surgical generator during use could inadvertently couple to the distal tip of the connected device instead of a desired target. This could cause dielectric breakdown at the distal tip of the device, which may cause patient harm. GDT 134 may be used in such a scenario to safely dissipate the energy of the electrosurgical generator, thereby avoiding dielectric breakdown of the device. Additionally, in an event where GDT 134 is discharged, it is sometimes necessary to replace GDT 134 to ensure continued patient safety. By including GDT 134 on back wall 130 of second interposer assembly 120, for example, it is possible to replace GDT 134 by installing a new back wall 130 or interchanging second interposer assembly 120 with a new second interposer assembly 120.

Still referring to FIGS. 2B and 2C, the orientation, size, and location of the plurality of fasteners 133, the plurality of extensions 131 and fasteners 132, connectors 136, and GDT 134 may vary on back wall 130 according to various aspects of this disclosure.

Figure 2D:
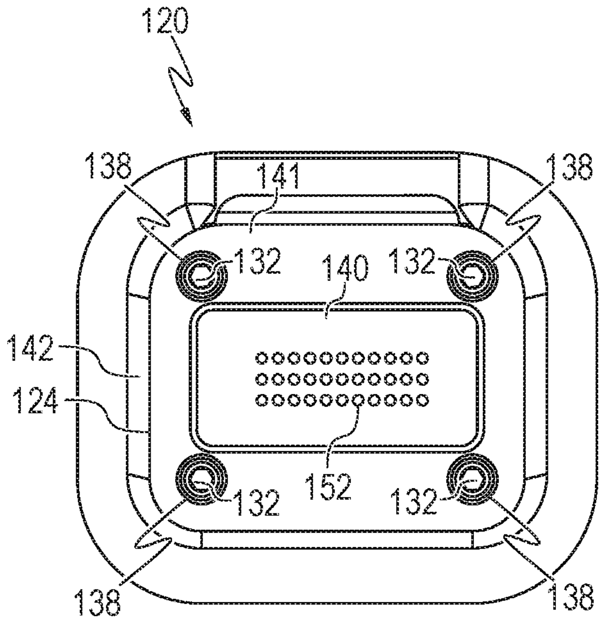
FIG. 2D illustrates a front view of the first interposer assembly shown in FIGS. 1, 2A, 2B, and 2C, according to aspects of this disclosure.
Figure 3:
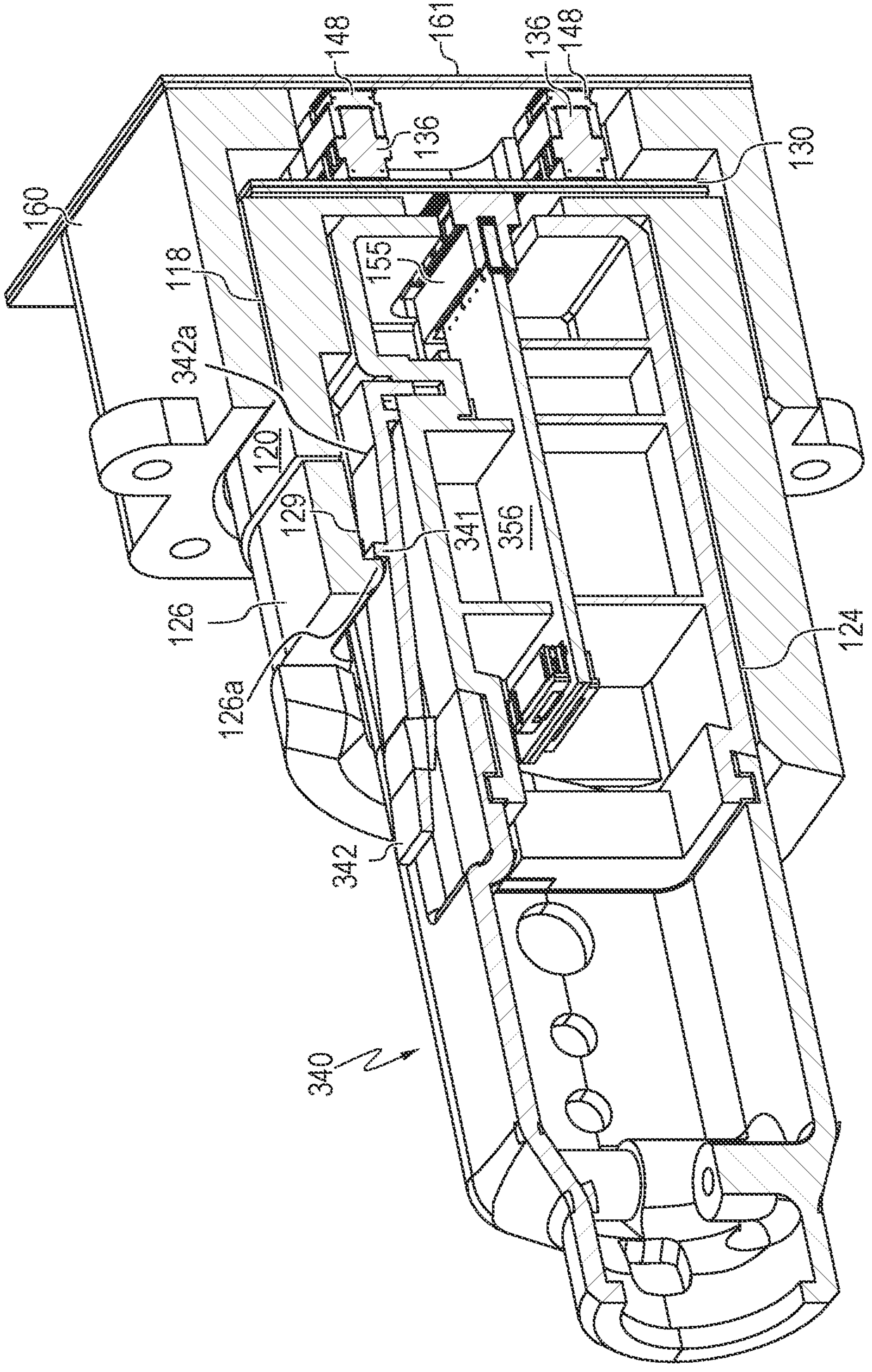
FIG. 3 illustrates a cross-sectional view of exemplary components of a medical device, interposer assembly, and a portion of the controller, according to aspects of this disclosure.

FIG. 2D shows a front view of second interposer assembly 120, looking into and through connector socket 124. As previously described, connector socket 124 extends through interposer housing 122 along center axis A of interposer housing 122 to a socket wall 141. In this configuration, center axis A extends perpendicularly into and out of the page. A bevel 142 (i.e. a chamfer) may extend around the inside, front edge of interposer housing 122 about connector socket 124 to guide a device connector (not shown) during insertion.

A plurality of counter-bored holes 138 on socket wall 141 may accept fasteners 132, shown in FIG. 2B. Fasteners 132 may be accessed by a user through the connector socket 124. Socket wall 141 may further comprise a spring pin mount 140 and a plurality of spring pins 152. Spring pin mount 140 and spring pins 152 are electrically coupled to the interposer PCBA, and the interposer PCBA may comprise, or may be contained within, back wall 130, as shown in FIGS. 2B and 2C. Accordingly, the electrical connection between spring pin mount 140, spring pins 152 and the interposer PCBA of second interposer assembly 120 may help to enable an electrical connection between second interposer assembly 120 and a device connector (not shown). The electrical connection between second interposer assembly 120 and the device connector (not shown) enables a user to control one or m ore electrical features of the device, such as an imaging sensor, illumination source, or other operative controls, when second interposer assembly 120 is connected to controller 110.

Although of different size, it shall be understood that first interposer assembly 116 may contain any or all of the previously described components and/or features from FIGS. 2A-2D and 3.

FIG. 3 demonstrates a cross-sectional view of second interposer assembly 120 within a portion 160 of controller 110 (shown in FIG. 1) and a device connector 340 connected to second interposer assembly 120. Device connector 340 of this exemplary embodiment further comprises a device PCBA 356. Device PCBA 356 is shaped like a thin card with its thickness oriented perpendicular to a longitudinal axis of device connector 340. Device PCBA 356 may be oriented within device connector 340 such that, upon insertion of device connector 340 into second interposer assembly 120, device PCBA 356 is inserted into an interposer PCBA connector 155, thereby creating a mechanical and electrical connection between the two components. Interposer PCBA connector 155 may be fixed to a front face of back wall 130 of second interposer assembly 120, and interposer PCBA connector 155 may be configured to receive device PCBA 356 of device connector 340.

One or more connectors 136 (described above with regard to FIGS. 2B and 2C) may be fixed to a rear face of back wall 130 of second interposer assembly 120. The one or more connectors 136 may be configured to be removably coupled to one or more controller connectors 148 of controller 110, for example, when second interposer assembly 120 is inserted into controller 110 through second port 118. Controller connectors 148 may be fixedly coupled to a controller PCBA 161 within controller 110 and extend perpendicularly outward from a front face of controller PCBA 161. Controller PCBA 161 may be coupled or oriented adjacent to portion 160 of controller 110.

Device connector 340 may be inserted into connector socket 124 of second interposer assembly 120. A device connector tab 342 may be movably coupled to device connector 340 such that the device connector tab 342 bends at a living hinge 342*a*, permitting device connector tab 342 to move radially inward and outward of second interposer assembly 120, for example, relative to the longitudinal axis of device connector 340.

Upon insertion of device connector 340 into second interposer assembly 120, a user may apply pressure radially inward to a free end of device connector tab 342, permitting a protrusion 341 protruding away from device connector tab 342 to slide under a radially inward flange 126*a* of latch 126 of second interposer assembly 120. Upon device PCBA 356 connecting to interposer PCBA connector 55, pressure may be released from device connector tab 342, allowing device connector tab 342 to bend radially outward, so that protrusion 341 rests under latch 126. Radially inward flange 126*a* prevents, or inhibits, device connector 340 from being inadvertently removed from controller 110 during use. To remove device connector 340 from second interposer assembly 120 and controller 110, a user may apply radially inward pressure to the free end of device connector tab 342, allowing protrusion 341 to be slid under radially inward flange 126*a* of latch 126. In such a way, device connector 340 may be removed from second interposer assembly 120.

Figure 4:
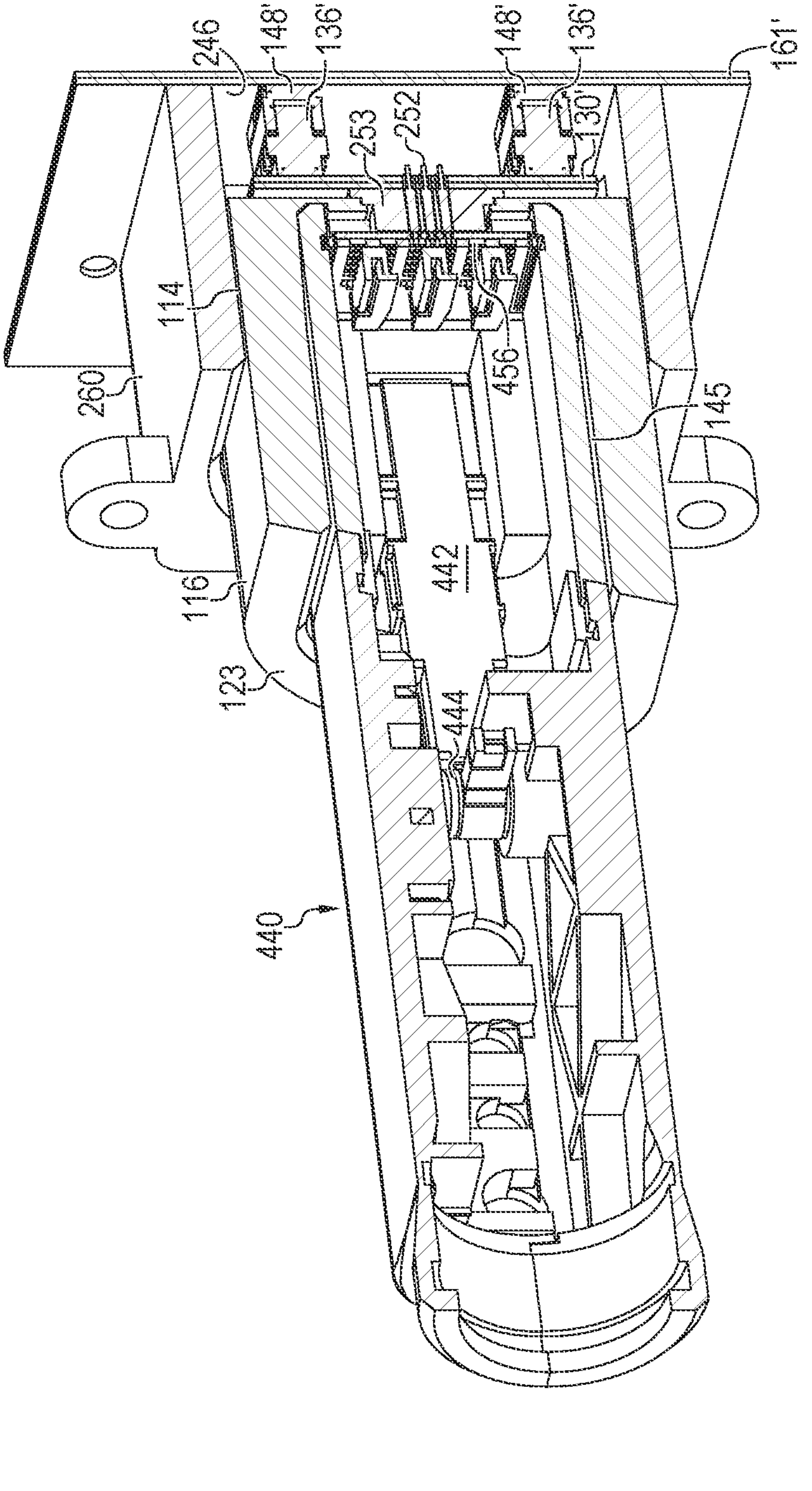
FIG. 4 illustrates a cross-sectional view of an alternative embodiment of exemplary components of a medical device, a second interposer assembly, and a portion of the controller, according to aspects of this disclosure.

FIG. 4 demonstrates a cross-sectional view of first interposer assembly 116 within a portion 260 of controller 110 (shown in FIG. 1) and an alternative embodiment of a device connector 440 connected to first interposer assembly 116. As discussed above, first interposer assembly 116 may be removably coupled to controller 110, through first port 114. Device connector 440 may be removably coupled to first interposer assembly 116 by means of one or more latches 442 and one or more springs 444. Spring(s) 444 may be coil spring(s) configured to push latch 442 radially outward, such that a portion of latch 442 is removably coupled to an internal portion of first interposer assembly 116, similarly to how device connector tab 342 is removably coupled to latch 126, described above with reference to FIG. 3. Accordingly, to remove device connector 440 from first interposer assembly 116, a user may press one or more latches 442 towards a center axis of device connector 440.

Device connector 440 of this exemplary embodiment further comprises a device PCBA 456. Device PCBA 456 may be oriented within device connector 440 such that, upon insertion of device connector 440 into first interposer assembly 116, for example, through a connector socket 145 of first interposer assembly 116, a plurality of pins 252 on a pin mount 253 of first interposer assembly 116 contact electrical pads on a face of device PCBA 456 of device connector 440, thereby creating an electrical connection between controller 110 and device connector 440.

Connector socket 145 is a space within first interposer assembly 116 and extends from a front face 123 of first interposer assembly 116, along a center axis of first interposer assembly 116, to a back wall 130' at a rear of first interposer assembly 116. Back wall 130' may be comprised of or include an interposer PCBA. Accordingly, back wall 130', and thus the interposer PCBA, may be in electrical contact with pins 252 to provide for an electrical connection between first interposer assembly 116 and controller 110.

Similar to connector(s) 136 discussed above with regards to second interposer assembly 120, one or more connectors 136' may be fixed to a rear surface of back wall 130' of first interposer assembly 116 such that, for example, connector(s) 136' are in electrical or physical contact with the interposer PCBA comprising or within back wall 130'. The one or more connectors 136' may be removably coupled to one or more controller connectors 148'. Controller connectors 148' may comprise any or all of the features of controller connectors 148 discussed above with respect to FIG. 3. Further, one or more controller connectors 148' are fixed to controller PCBA 161' and, thus, may extend outwardly from a surface 246 of controller PCBA 161'. Thus, when first interposer assembly 116 is inserted into controller 110, connector(s) 136' are electrically and mechanically coupled to controller connector(s) 148'.

Further, when device connector 440 is inserted into first interposer assembly 116, device PCBA 456 may be electrically and/or mechanically coupled with the plurality of pins 252. For example, plurality of pins 252 may be configured to extend into corresponding holes of device PCBA 456 to provide for an electrical connection between device PCBA 456 and first interposer assembly 116. Additionally or alternatively, plurality of pins 252 may be configured to contact device PCBA 456 such that device PCBA 456 is electrically coupled to pins 252 and, thus, first interposer assembly 116. Accordingly, device connector 440 may be electrically coupled to controller 110 via first interposer assembly 116.

Figure 5:
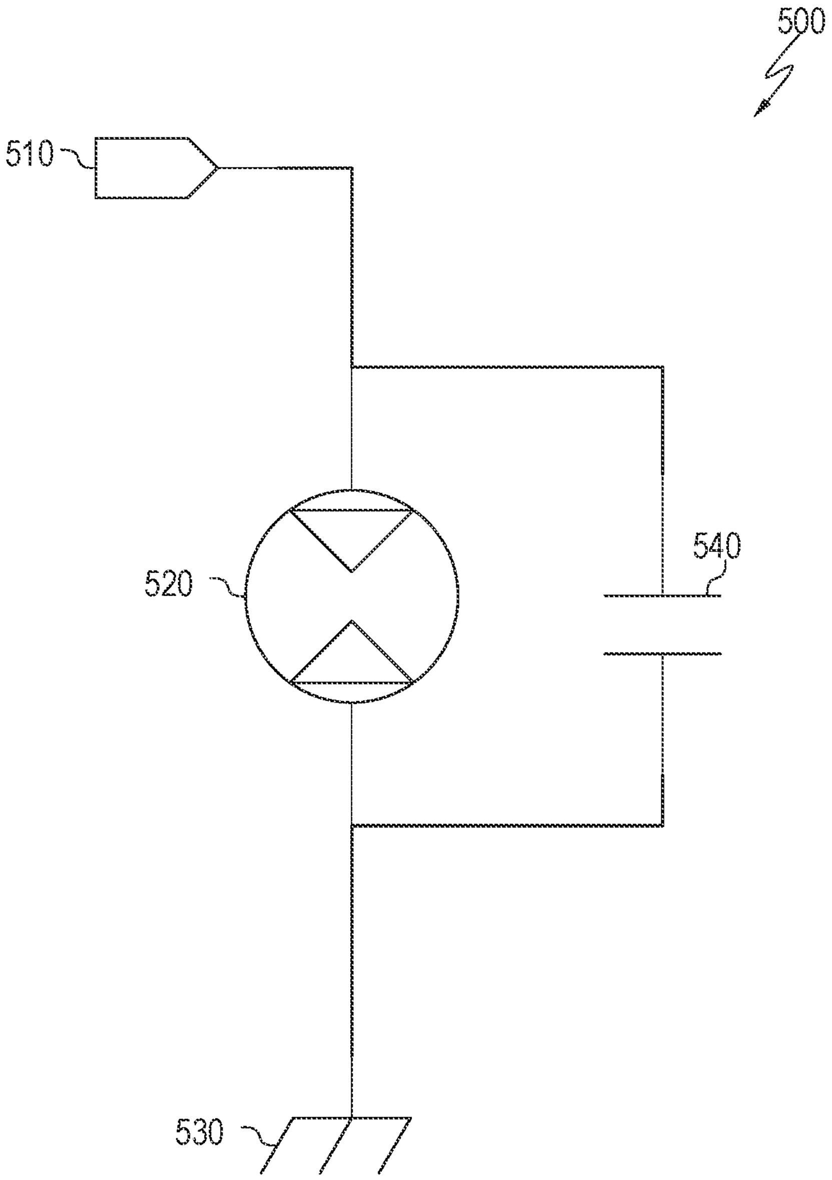
FIG. 5 illustrates an exemplary circuit of a gas discharge tube (GDT) return path, according to aspects of this disclosure.

FIG. 5 shows an exemplary circuit 500 for the connection of a GDT 520 to a controller's ground 530. For example, exemplary circuit 500 may be used with medical system 100 shown in FIG. 1. GDT 520 may be used to safely dissipate the energy of an electrosurgical generator and avoid a dielectric breakdown of a connected device. Circuit 500 includes GDT 520 and a capacitor 540 in parallel. GDT 520 and capacitor 540 are electronically connected to the PCBA comprising or within back wall 130' of first interposer assembly 116 or back wall 130 of second interposer assembly 120, for example, by PCBA connection 510. GDT 520 and capacitor 540 are also electronically connected to a ground 530 of controller 110. Accordingly, an electrical current travels from PCBA connection 510 through GDT 520 and capacitor 540 through to ground 530 in controller 110.

In embodiments, capacitor 540 may be a 5 kV, 470 pF capacitor. With this configuration, any inadvertent coupling of a high frequency surgical generator to a connected device, such as, for example, an endoscope will safely dissipate through GDT 520. Further, by including GDT 520 on removable first interposer assembly 116 and/or second interposer assembly 120, as shown in FIGS. 2B and 2C, it is possible to quickly and safely replace GDT 520, for example, by installing a new first interposer assembly 116 and/or a new second interposer assembly 120 or by installing a new back wall 130 within second interposer assembly 120 or a new back wall 130' within first interposer assembly 116.

It also should be understood that any of the medical systems and devices described herein may be used in various therapeutic and diagnostic medical procedures where the use of a controller is necessary. Such procedures may include a Esophago-gastro-duodenoscopy (EGD), a colonoscopy, Endoscopic Submucosal Dissection (ESD), cancer treatment, kidney or bladder biopsies or resections, other procedures where an endoscope and a controller is needed, or any other therapeutic or diagnostic procedure. By, for example, having a reliable electrical and mechanical connection between a medical device (e.g. a scope) and a controller, embodiments discussed herein, may help reduce procedure time, increase tissue treatment effectiveness, reduce the risks to the subject, etc.

Although the exemplary embodiments described above have been disclosed in connection with medical systems comprising a controller and at least one interchangeable interposer, a person skilled in the art will understand that the principles set out above can be applied to any medical device or medical method and can be implemented in different ways without departing from the scope of the disclosure as defined by the claims. In particular, constructional details, including manufacturing techniques and materials, are well within the understanding of those of skill in the art and have not been set out in any detail here. These and other modifications and variations are well within the scope of this disclosure and can be envisioned and implemented by those of skill in the art.

Moreover, while specific exemplary embodiments may have been illustrated and described collectively herein, it should be appreciated that any subsequent arrangement designed to achieve the same or similar purpose may be substituted for the specific embodiments described and shown herein. This disclosure is intended to cover any and all subsequent adaptations or variations of various embodiments. Combinations of the above embodiments, and other embodiments not specifically described herein, will be apparent to those of skill in the art upon reviewing the description.

While principles of the disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

Other exemplary embodiments of this disclosure will be apparent to those skilled in the art from consideration of the specification and practice of the exemplary embodiments disclosed herein. It is intended that the specification and examples be considered as exemplary only, and departures in form and detail may be made without departing from the scope and spirit of this disclosure as defined by the following claims.

We claim:

1. An interposer assembly for connecting a medical device to a controller, the interposer assembly comprising:

a housing defining a front-facing socket for removably receiving a connector of the medical device and including a slot for receiving a latch, the latch including a protrusion for inhibiting inadvertent removal of the connector of the medical device from the front-facing socket, at least one electrical connector on a rear face of the housing, the at least one electrical connector for removable connection to the controller, and a printed circuit board assembly (PCBA) at least partially enclosed within the housing and electrically connected to the at least one electrical connector.

2. The interposer assembly of claim 1, further comprising at least one mechanical fastener on the rear face of the housing, the at least one mechanical fastener for removable connection to the controller.

3. The interposer assembly of claim 2, wherein access to the at least one mechanical fastener is through the front-facing socket of the housing.

4. The interposer assembly of claim 2, wherein the at least one mechanical fastener includes a plurality of screws.

5. The interposer assembly of claim 1, further comprising a gas discharge tube extending from the rear face of the housing.

6. The interposer assembly of claim 5, wherein a circuit of the gas discharge tube comprises a capacitor in parallel to the gas discharge tube, and wherein the circuit is for electrical connection to a ground connection within the controller.

7. The interposer assembly of claim 1, wherein the latch is removable from the housing via one or more latch fasteners.

8. The interposer assembly of claim 1, wherein the protrusion protrudes radially inward towards the front-facing socket and includes a rear-facing surface for contact with the connector of the medical device, to inhibit advertent removal of the connector of the medical device from the front-facing socket.

9. The interposer assembly of claim 1, wherein the PCBA is removably connected to the housing via one or more PCBA connectors.

10. The interposer assembly of claim 1, wherein a front-facing wall of the housing includes a circuit board connector for receipt of a circuit board of the connector of the medical device.

11. The interposer assembly of claim 1, further comprising a spring pin mount on a front-facing wall of the housing, the spring pin mount for electrical connection to the connector of the medical device.

12. The interposer assembly of claim 1, wherein the housing has a shape corresponding to a shape of a port of the controller.

13. The interposer assembly of claim 1, wherein a rear wall of the housing, that includes the rear face of the housing, is one of:

comprised of the PCBA; or a panel enclosing the PCBA.

14. The interposer assembly of claim 1, wherein:

the protrusion of the latch is a radially inward flange formed from a recessed inner surface of the housing comprising the slot, and a rear-facing surface of the radially inward flange is for receiving a connector protrusion extending radially outward from the connector of the medical device after a pressure, applied to insert the connector of the medical device into the front-facing socket of the housing and causing the connector to slide under the radially inward flange and into the recessed inner surface of the housing, is released.

15. A medical system, comprising:

a controller including a first port and a second port;

a first interposer assembly, wherein the first interposer assembly is configured to be removably coupled to the controller through the first port and removably receive a connector of a first medical device; and a second interposer assembly separate from the first interposer assembly, wherein the second interposer assembly is configured to be removably coupled, separately from the first interposer assembly, to the controller through the second port and removably receive a connector of a second medical device.

16. The medical system of claim 15, wherein at least one of the first interposer assembly or the second interposer assembly comprises:

a housing defining a front-facing socket for removably receiving the connector of the one of the first medical device or the second medical device, respectively, and at least one electrical connector on a rear face of the housing, the at least one electrical connector for removable connection to the controller.

17. The medical system of claim 16, wherein at least one of the first interposer assembly or the second interposer assembly further comprises at least one mechanical fastener on the rear face of the housing, the at least one mechanical fastener for removable connection to the controller, and wherein access to the at least one mechanical fastener is through the front-facing socket of the housing.

18. The medical system of claim 15, further comprising the first medical device, and wherein the first interposer assembly further comprises a latch including a protrusion that protrudes radially inward towards a socket and includes a rear-facing surface for contact with the connector of the first medical device, to inhibit removal of the connector of the first medical device from the socket.

19. A method for connecting a medical device to a controller, the method comprising:

inserting a connector of the medical device into a socket of an interposer assembly, the interposer assembly positioned in a port of the controller via a releasable connection; and inhibiting inadvertent removal of the connector from the socket via a latch of the interposer assembly, wherein a housing of the interposer assembly defining the socket includes a slot for receiving the latch, the latch comprising a first protrusion for releasably engaging a second protrusion extending radially outward from the connector.

* * * * *